(12) United States Patent
Law

(10) Patent No.: US 8,053,600 B2
(45) Date of Patent: Nov. 8, 2011

(54) PROCESS FOR THE PREPARATION OF CARBOXYLIC ACIDS AND/OR DERIVATIVES THEREOF

(75) Inventor: David John Law, Beverley (GB)

(73) Assignee: BP Chemicals Limited, Middlesex (GB)

( * ) Notice: Subject to any disclaimer, the term of this patent is extended or adjusted under 35 U.S.C. 154(b) by 344 days.

(21) Appl. No.: 12/226,137

(22) PCT Filed: Mar. 27, 2007

(86) PCT No.: PCT/GB2007/001095
§ 371 (c)(1),
(2), (4) Date: Oct. 9, 2008

(87) PCT Pub. No.: WO2007/116201
PCT Pub. Date: Oct. 18, 2007

(65) Prior Publication Data
US 2009/0275774 A1    Nov. 5, 2009

(30) Foreign Application Priority Data
Apr. 12, 2006   (GB) .................................. 0607395.1

(51) Int. Cl.
*C07C 51/12* (2006.01)
*C07C 51/10* (2006.01)
*B01J 29/00* (2006.01)

(52) U.S. Cl. ............................ 562/519; 562/517; 502/74
(58) Field of Classification Search ....................... None
See application file for complete search history.

(56) References Cited

U.S. PATENT DOCUMENTS
4,612,387 A    9/1986 Feitler
5,420,345 A *  5/1995 Smith ........................... 562/519

OTHER PUBLICATIONS

Drozdova et al, Journal of Physical Chemistry, Bonding of Co Ions in ZSM-5, Ferrierite, and Mordenite: An X-ray Absorption, UV-Vis and IR Study, 2002, 106 pp. 2240-2248.*
Urata et al, Tetrahedron Letters, Transition Metal Complex Catalyzed Carbonylation of Organic Halides in the Presence of Molecular Sieves Instead of Base, 1991, 32(36), pp. 4733-4736.*
International Search Report for PCT/GB2007/001095, mailed Jun. 25, 2007.
Written Opinion of the International Searching Authority for PCT/GB2007/001095, mailed Jun. 25, 2007.

* cited by examiner

*Primary Examiner* — Paul A Zucker
(74) *Attorney, Agent, or Firm* — Nixon & Vanderhye

(57) ABSTRACT

Process for preparing an aliphatic carboxylic acid having (n+1) carbon atoms, where n is an integer up to 6, and/or an ester or anhydride thereof by contacting an aliphatic alcohol having n carbon atoms and/or a reactive derivative thereof with carbon monoxide under hydrous conditions in the presence of a ferrierite catalyst.

23 Claims, No Drawings

PROCESS FOR THE PREPARATION OF CARBOXYLIC ACIDS AND/OR DERIVATIVES THEREOF

This application is the U.S. national phase of International Application No. PCT/GB2007/001095, filed 27 Mar. 2007, which designated the U.S. and claims priority to GB Application No. 0607395.1, filed 12 Apr. 2006, the entire contents of each of which are hereby incorporated by reference.

This invention relates to a process for preparing an aliphatic carboxylic acid and/or derivatives thereof by reacting the corresponding alcohol and/or a reactive derivative thereof with carbon monoxide in the presence of a catalyst comprising ferrierite.

The preparation of acetic acid from methanol and carbon monoxide is a well known carbonylation process and is one which is carried out commercially. On a commercial scale the manufacture of acetic acid may be operated as a homogeneous liquid-phase process in which the carbonylation reaction is catalysed by a soluble rhodium/iodide complex and an alkyl iodide such as methyl iodide. The main drawbacks of this process are the use of iodide which can lead to corrosion problems and the difficulties associated with separation of the products and catalyst components from a single phase. Both of these drawbacks could be overcome if a heterogeneous process using an iodide free solid catalyst could be developed.

GB 1185453 discloses certain multiphase catalysts comprising a catalytically active metal including inter alia copper, rhodium and iridium supported on a wide range of carrier materials including silicas, aluminas, carbons, zeolites, clays and polymers. These multiphase catalysts are taught as being useful in the heterogeneous gas phase carbonylation of methanol to acetic acid in the presence of a halide promoter. A similar process is disclosed GB 1277242, although neither patent exemplifies the use of zeolites in such a process.

U.S. Pat. No. 4,612,387 discloses a process for making monocarboxylic acids and esters comprising contacting carbon monoxide with a monohydric alcohol having from 1 to 4 carbon atoms in the presence of a crystalline aluminosilicate zeolite having a silica to alumina ratio of at least about 6 and a constraint index within the range of 1 to 12 under a pressure of at least 1 atmosphere. The most preferred zeolites according to this definition are ZSM-5, ZSM-11, ZSM-12, ZSM-38 and ZSM-35 with ZSM-5 being particularly preferred.

J Catalysis, 71, 233-43 (1981) discloses the use of photoelectron spectroscopy (ESCA) to determine the activity of a rhodium mordenite catalyst and other supported rhodium catalysts towards carbonylation of methanol to acetic acid.

Angew. Chem. Int. Ed 2006, 45, 1617-1620 describes dimethyl ether carbonylation to methyl acetate at low temperatures in the presence of certain halide-free zeolite catalysts. This paper exemplifies the hydrous carbonylation of dimethyl ether in the presence of mordenite and the anhydrous carbonylation of dimethyl ether using ferrierite.

EP 0596632 A1 discloses a process for the preparation of an aliphatic carboxylic acid by contacting an alcohol or a reactive derivative thereof with carbon monoxide, substantially in the absence of halogens or derivative thereof, in the presence of a catalyst consisting essentially of a mordenite zeolite which has been ion-exchanged or loaded with copper, nickel, iridium, rhodium or cobalt, characterised in that the process is carried out at a temperature in the range 300° to 600° C. and at a pressure in the range 15 to 200 bars.

Thus there remains a need for an improved heterogeneous process for preparing carboxylic acids and/or derivatives thereof from alcohols and/or reactive derivatives thereof and carbon monoxide.

It has now been found that a heterogeneous carbonylation process employing a ferrierite zeolite (hereinafter referred to as ferrierite) as catalyst provides significant selectivities to carbonylation products (the carboxylic acid and/or derivatives thereof).

Accordingly, the present invention provides a process for preparing an aliphatic carboxylic acid having (n+1) carbon atoms, where n is an integer up to 6, and/or an ester or anhydride thereof which comprises contacting an aliphatic alcohol having n carbon atoms and/or a reactive derivative thereof with carbon monoxide under hydrous conditions in the presence of a ferrierite catalyst.

Using ferrierite as the catalyst in the process of the present invention, high selectivities to carbonylation products can be achieved with low hydrocarbon by-product formation such as $C_1$-$C_{12}$ alkanes, alkenes and polymethylated aromatic hydrocarbons.

In the process of the present invention an aliphatic alcohol or a reactive derivative thereof is carbonylated with a carbon monoxide. The process is particularly applicable to aliphatic alcohols having up to 6, such as up to 3, carbon atoms. A preferred alcohol is methanol.

Reactive derivatives of the alcohol which may be used as an alternative to, or in addition to the alcohol, include dialkyl ethers, esters of the alcohol and alkyl halides. Suitable reactive derivatives of methanol, for example, include methyl acetate, dimethyl ether and methyl iodide. A mixture of an alcohol and the reactive derivative thereof, for example a mixture of methanol and methyl acetate, may also be employed.

The product of the carbonylation process may be an aliphatic carboxylic acid and/or the ester of the aliphatic carboxylic acid. For example, where the alcohol is methanol the product predominantly comprises acetic acid but it may also comprise some methyl acetate. Where an ester is a product, it may be converted to the corresponding carboxylic acid by known methods, for example by hydrolysis using reactive distillation.

The process of the present invention is carried out under hydrous conditions. The feed comprising an alcohol, ester or ether or any combination thereof may contain water. Suitably, where an alcohol such as methanol is used as the feed, the molar ratio of water to alcohol is in the range 10:1 to 1:1 such as 3:1 or 1:1. Where an ester or ether reactive derivative such as methyl acetate or dimethyl ether, is used as the feed, the molar ratio of water to ester or ether is suitably in the range 10:1 to 1:1, such as 2:1 and 1.5:1.

The water may be fed separately to or together with the alcohol and/or reactive derivative. The water may be present in liquid or vapour form.

Alternatively, depending on the nature of the feed, water may be generated in-situ, for example by the dimerisation of alcohol feed to ethers or via esterification of methanol and acetic acid product. Suitably, the amount of generated water may be such that the ratio of alkyl groups derived from the alcohol or ester or ether feed to water is less than or equal to 1.

The purity of the carbon monoxide used is not deemed to be especially critical. The carbon monoxide may comprise substantially pure carbon monoxide, for example, carbon monoxide typically provided by suppliers of industrial gases or it may contain small amounts of impurities such as nitrogen and the noble gases which do not interfere with the conversion of the reactants to the desired carbonylation products. The carbon monoxide may be used in admixture with hydrogen. Suitably, the ratio of $CO:H_2$ is in the range 1:3 to 15:1 on a molar basis, such as 1:1 to 10:1. For example, mixtures of carbon monoxide and hydrogen as produced by the reforming or partial oxidation of hydrocarbons (synthesis gas) may also be used in the process of the present invention.

The catalyst used in the process of the present invention is a ferrierite zeolite. Ferrierite is a member of the aluminosilicate zeolite class of minerals with a formula generally given as $Na_{0.8}K_{0.2}MgSi_{15}Al_3O_{36.9}H_2O$ or $(Mg,Na_2,K_2,Ca)_{3-5}Mg[Al_{5-7}Si_{27.5-31}O_{72}]\cdot18H_2O$. It is available from a number of commercial sources of such materials. It is further characterised by having a constraint index of 8.2-10.5 and a silica to alumina ratio in the range 20-60. It is well known to those skilled in the art that the silica to alumina ratio may be increased by using de-illumination techniques, for example, by hydro-thermal treatment or acid leaching of the ferrierite. Ferrierite also possesses a characteristic X-ray powder diffraction pattern which will be well known to those skilled in the art. Additional information on ferrierite can be found on the website of the International Zeolite association, www.iza-online.org.

For the process of the present invention it is preferred that the ferrierite has a silica to alumina molar ratio in the range 10:1 to 30:1, most preferably in the range 15:1 to 25:1.

Optionally, the ferrierite may comprise one or more additional elements such as gallium, iron, boron, copper, silver, gold, nickel, cobalt, iridium and rhodium. Such elements may be present in its framework or may be loaded onto the ferrierite by known means. For example, the ferrierite may, in addition to silicon and aluminium atoms, contain further elements in its framework. Such framework modifier elements may be gallium, iron or boron. The framework modifier elements may be introduced into the framework by conventional methods, for example by hydrothermal synthesis. Suitable preparation techniques are described, for example, in EP-A-234 755 and Catalysis Today 110 (2005) pages 255-263. Where a framework modifier is used, the ferrierite may suitably have a molar ratio of silica to the oxide of the framework modifier element in the range 10:1 to 100:1.

The ferrierite may also be ion-exchanged or otherwise loaded with one or more metals such as copper, silver, nickel, iridium, cobalt or rhodium. The loading of the ferrierite by one or more metals may be by any method such as the well-known techniques of ion-exchange, impregnation and incipient wetness. If the ferrierite is to be ion-exchanged up to 100% of the cation-exchangeable sites on the ferrierite may be exchanged with the metal cations using well known techniques. It is preferred that the remaining cations in the exchanged ferrierite are protons hence it is convenient to start the exchange process from the ammonium or hydrogen form.

As an alternative to ion-exchange, the ammonium or hydrogen form of the ferrierite can be impregnated with solutions of one or more metal salts and subsequently dried. Preferably, the ferrierite is calcined, for example, in air, at high temperature such as 500-600° C., after metal loading or exchange. The amounts used are preferably such as to produce a catalyst having a metal content of 0.001 to 45.6% by weight based on the total catalyst such as 0.01-30% by weight. Alternatively, the metal loading may be expressed on the basis of exchangeable sites, which is generally taken to be equivalent to the moles of aluminium per unit volume or per unit weight of ferrierite. The metal loading may suitably be 1 to 100 mol % of exchangeable sites.

The ferrierite catalyst is activated prior to use by, for example, subjecting the ferrierite catalyst for at least one hour at elevated temperature under flowing nitrogen, carbon monoxide or hydrogen.

In practicing the carbonylation process, it may be desirable to mix the ferrierite catalyst with an inert material which is resistant to the temperature and other conditions employed in the process. Such materials include synthetic or naturally occurring substances as well as inorganic materials such as silica or carborundum.

Optionally, prior to feeding methanol over the catalyst, the methanol may be passed through a pre-bed, for example a pre-bed of gamma-alumina, at reaction temperature.

The process of the present invention is preferably carried out by passing methanol vapour and carbon monoxide gas through a fixed, fluidised or moving bed of the catalyst maintained at the desired temperature and pressure.

Preferably, the process of the present invention is carried out substantially in the absence of halides, such as iodide. By substantially is meant that the halide, for example, iodide content of the feed gases and catalyst are less than 500 ppm and preferably less than 100 ppm.

The process is suitably carried out at a temperature in the range 200 to 600° C., preferably 250 to 400° C.

The process is suitably carried out at a pressure in the range 10 to 200 barg, preferably 10 to 150 barg, such as 25 to 100 barg.

The molar ratio of carbon monoxide to the alcohol, such as methanol or reactive derivative thereof is suitably in the range 1:1 to 99:1, such as 1:1 to 30:1.

The Gas Hourly Space Velocity (GHSV) is suitably in the range 500 to 15,000 $h^{-1}$, such as 2000 to 10,000 $h^{-1}$.

The process may be carried out either as a fixed bed, fluid bed or moving bed process.

The process may be carried out as either a continuous or batch process, preferably continuous.

Essentially, the process is a gas-phase process with reactants being introduced in either liquid or gaseous phase and products withdrawn as gases. The carbonylation products may subsequently be cooled and condensed. Where methyl acetate is a product, it can be recovered from the reaction products and hydrolysed to form acetic acid. The acetic acid can be subsequently purified using conventional techniques, such as distillation.

The invention will now be illustrated with reference to the following Examples.

Catalyst Preparation
Preparation of Cu—H-MOR 50.02 g mordenite (ex Tosoh Corp.) having a silica:alumina ratio of 19 was treated with 0.033 moles of copper nitrate hemipentahydrate (ex Aldrich) dissolved in 50 ml of water. Approximately 10 ml of water was added to the mixture to form a mobile slurry. The mixture was stirred thoroughly avoiding the introduction of air into the mixture using a magnetic stirrer bar (approximately 200 rpm). Stirring was continued for 3 hours at ambient temperature. The resulting mixture was then dried with the aid of a rotary evaporator until a powder was obtained. The powder was then dried at 110° C. for 3 hours in air followed by calcination at 500° C. for 24 hours. After cooling the solid material was pressed using a 12 tonne press and a 32 mm die set, then lightly ground using a pestle and mortar to yield particle sizes of 0.5 to 1 mm. The mordenite contained 4 wt % copper (40 mol % copper as determined by inductively coupled plasma absorption spectroscopy (ICP)).

Preparation of H-FER

Approximately 50 g ammonium ferrierite (ex Zeolyst International, CP914C.) having a silica:alumina ratio of 20 was dried at 110° C. for 3 hours in air followed by calcination at 500° C. in air for 24 hours. After cooling the solid material was pressed using a 12 tonne press and a 32 mm die set, then lightly ground using a pestle and mortar to yield particle sizes of 0.5 to 1 mm.

Preparation of Cu—H-FER 50.27 g ammonium ferrierite (ex Zeolyst International, CP914C.) having a silica:alumina ratio of 20 was treated with 0.033 moles of copper nitrate hemipentahydrate (ex Aldrich) dissolved in 50 ml of water. Approximately 10 ml of water was added to the mixture to form a mobile slurry. The mixture was stirred thoroughly avoiding the introduction of air into the mixture using a magnetic stirrer bar (approximately 200 rpm). Stirring was continued for 3 hours at ambient temperature. The resulting mixture was then dried with the aid of a rotary evaporator until a powder was obtained. The powder was then dried at 110° C. for 3 hours in air followed by calcination at 500° C. in air for 24 hours. After cooling the solid material was pressed using a 12 tonne press and a 32 mm die set, then lightly ground using a pestle and mortar to yield particle sizes of 0.5 to 11 mm.

Preparation of Ag—H-FER 17.03 g ammonium ferrierite (ex Zeolyst International, CP914C.) having a silica:alumina ratio of 20 was treated with 0.0065 moles of silver nitrate (ex Aldrich) dissolved in 50 ml of water. The mixture was stirred thoroughly avoiding the introduction of air into the mixture using a magnetic stirrer bar (approximately 200 rpm). Stirring was continued for 3 hours at ambient temperature. The resulting mixture was then dried with the aid of a rotary evaporator until a powder was obtained. The powder was then dried at 110° C. for 18 hours in air followed by calcination at 500° C. in air for 24 hours. After cooling the solid material was pressed using a 13 tonne press and a 32 mm die set, then lightly ground using a pestle and mortar to yield particle sizes of 0.5 to 1 mm.

Methanol Carbonylation

The carbonylation reactions were conducted in a single tube fixed bed reactor of approximately 13 mm diameter. For each reaction 5 ml of catalyst was diluted in a ratio of 1:5 with 25 ml of silica beads of equivalent particle size to ensure complete mixing. In Examples 1-4 (but not Example 1a) a gamma-alumina pre-bed of approximately 10 ml in volume was employed. After loading of the catalyst (and where used, the pre-bed) into the reactor, the reactor was pressurised to reaction pressure (30 barg) with nitrogen and subsequently heated to reaction temperature (300° C.). The catalyst bed was then pre-treated with carbon monoxide at reaction pressure and temperature for 2 hours. After pre-1-treatment, hydrogen, carbon monoxide and methanol were fed to the reactor and the reaction was left to run for up to 24 hours. After this time, the feed gases were stopped and the reactor cooled by nitrogen and then vented. Water was generated in-situ by the dimerisation of the methanol to ether and by esterification of methanol with the product acetic acid.

Gaseous products were analysed online by an Agilent 3000 gas chromatograph fitted with 3 Agilent column modules and 3 thermal conductivity detectors. Liquid products were collected in a liquid collection knock-out pot at 7° C. and analysed at intervals on a Chrompack CP9000 gas chromatograph fitted with a Chrompack CP-Wax 52 column and a flame ionisation detector.

Each reaction was carried out at 3000 GHSV and with a ratio of CO:methanol of 9:1.

The results of the experiments are given in Table 1 below. The selectivities to acetyls products were calculated according to the formula:

$$([AcOH]out+[MeOAc]out+[EtOAc]out) \times 100 / ([CH_4]out+[AcOH]out+[MeOAc]out+[ACH]out+[EtOH]out+2\times[EtOAc]out+2\times[Acetone]out+\Sigma(nx[C_{n=2\,to\,12}]out)$$

where

AcOH is acetic acid; MeOAc is methyl acetate; EtOAc is ethyl acetate; CH4 is methane; AcH is acetaldehyde and EtOH is ethanol. All components are expressed in moles.

TABLE 1

| Example | Time on stream (hrs) | Methane (g/l/hr) | Hydrocarbons ($C_2$-$C_{12}$) (g/l/hr) | MeOAc (g/l/hr) | AcOH (g/l/hr) | Acetyls Selectivity (%) |
|---|---|---|---|---|---|---|
| 1 H—FER | 3 | 1.7 | 4.2 | 68 | 20 | 75 |
|  | 12 | 0.4 | 0.3 | 36 | 8 | 93 |
|  | 24 | 0.2 | 0.1 | 13 | 1 | 92 |
| 1a H—FER (no pre-bed) | 3 | 1.5 | 4.5 | 66 | 20 | 75 |
|  | 12 | 0.5 | 0.3 | 36 | 8 | 93 |
|  | 24 | 0.2 | 0.1 | 17 | 3 | 95 |
| 2 Cu—H—FER | 3 | 0.7 | 7.3 | 62 | 11 | 64 |
|  | 12 | 0.5 | 2.8 | 58 | 11 | 80 |
|  | 24 | 0.1 | 1.9 | 24 | 4 | 74 |
| 3 Ag—H—FER | 3 | 1.5 | 8.2 | 77 | 15 | 66 |
|  | 12 | 0.3 | 0.1 | 32 | 8 | 97 |
|  | 24 | 0.2 | 0 | 20 | 3 | 64 |
| 4 Cu—H-MOR | 3 | 3.8 | 40 | 31 | 64 | 34 |
|  | 12 | 2.9 | 48 | 55 | 30 | 25 |
|  | 24 | 2.3 | 23 | 38 | 18 | 31 |

The invention claimed is:

1. A process for preparing acetic acid and/or methyl acetate, said process comprising contacting methanol and/or a reactive derivative thereof selected from the group consisting of dimethyl ether and methyl acetate with carbon monoxide under hydrous conditions in the presence of a ferrierite catalyst.

2. A process according to claim 1 wherein the ferrierite has a silica:alumina molar ratio in the range 10:1 to 30:1.

3. A process according to claim 2 wherein the ferrierite has a silica:alumina molar ratio in the range 15:1 to 25:1.

4. A process according to claim 1 wherein the ferrierite is ion-exchanged or otherwise loaded with at least one metal selected from copper, silver, nickel, iridium, cobalt and rhodium.

5. A process according to claim 4 wherein the ferrierite is ion-exchanged or otherwise loaded with at least one metal selected from copper and silver.

6. A process according to claim 4 wherein the metal loading is in the range 1 to 100 mol % per unit volume of aluminium.

7. A process according to claim 1 wherein the ferrierite comprises a framework modifier element selected from at least one of gallium, iron and boron.

8. A process according to claim 7 wherein the ferrierite has a silica:oxide of the framework modifier element molar ratio in the range 10:1 to 100:1.

9. A process according to claim 1 wherein the ferrierite catalyst is activated prior to use.

10. A process according to claim 9 wherein the ferrierite is activated by contacting it with at least one of nitrogen, carbon monoxide and air, for at least 1 hour at elevated temperature.

11. A process according to claim 1 wherein water is fed separately to or together with the alcohol and/or reactive derivative.

12. A process according to claim 11 wherein the molar ratio of water:alcohol is in the range 10:1 to 1:1.

13. A process according to claim 11 wherein the molar ratio of water to ester or ether reactive derivative is in the range 10:1 to 1:1.

14. A process according to claim 13 wherein the molar ratio of water:ester or ether is 2:1.

15. A process according to claim 1 wherein hydrogen is also fed to the process.

16. A process according to claim 1 wherein the process is carried out at a temperature in the range 200 to 600° C.

17. A process according to claim 1 wherein the process is carried out at a pressure in the range 10 to 200 barg.

18. A process according to claim 1 wherein the molar ratio of carbon monoxide to the alcohol or reactive derivative is in the range 1:1 to 99:1.

19. A process according to claim 1 wherein the gas hourly space velocity is in the range 500 to 15,000 $h^{-1}$.

20. A process according to claim 1 wherein the process is carried out as a fixed bed, fluidised bed or moving bed process.

21. A process according to claim 1 wherein the process is operated as a continuous process.

22. A process according to claim 1 wherein the process is carried out substantially in the absence of halides.

23. A process according to claim 1 wherein acetic acid is prepared by contacting methanol with carbon monoxide in the presence of a ferrierite catalyst selected from H-ferrierite, ferrierite loaded with silver and ferrierite loaded with copper.

* * * * *